United States Patent [19]

Wallace et al.

[11] Patent Number: 5,166,317
[45] Date of Patent: Nov. 24, 1992

[54] NEUROTROPHIC FACTOR

[75] Inventors: Thomas L. Wallace; David E. Potter; Craig E. Crosson, all of The Woodlands, Tex.

[73] Assignee: Houston Biotechnology Incorporated, The Woodlands, Tex.

[21] Appl. No.: 265,043

[22] Filed: Oct. 31, 1988

[51] Int. Cl.$^5$ ............ A61K 37/02; C07K 3/02; C07K 3/12; C07K 15/06
[52] U.S. Cl. .................. 530/350; 530/416; 530/417; 530/848
[58] Field of Search ............ 530/350, 413, 416, 417, 530/848; 514/21

[56] References Cited

U.S. PATENT DOCUMENTS 4,923,696 5/1990 Appel et al. .............. 530/350
4,997,929 3/1991 Collins et al. ............ 536/27
5,011,914 4/1991 Collins et al. ............ 530/399

FOREIGN PATENT DOCUMENTS 0233838 1/1987 European Pat. Off.

OTHER PUBLICATIONS

Chemical Abstracts 109:67650f (1988), abstracting Hofmann, "Ciliary neuronotrophic factor stimulates choline acetyltrasferase activity in cultured chicken retina neurons", *J. Neurochem.*, 1988, 51(1), 109–13.

Angeletti, et al., "Subunit Structure and Amino Acid Composition of Mouse Submaxillary Gland Nerve Growth Factor", *Biochemistry*, vol. 10, No. 3 (1971) pp. 463–469.

Lin, et al., "Purification, Cloning and Expression of Ciliary Neurotrophic Factor (CNTF)", *Research Articles*, Nov. 24, 1989, pp. 1023–1025.

Levi-Montalcini, *Science* (1987) 237:1154–1162.

Barde, et al., *EMBO Journal* (1982) 1:549–553.

Gaspodarowicz, et al., *Proc. Natl. Acad. Sci. USA* (1984) 81:6963–6967.

Barbin, et al., *Journal of Neurochemistry* (1984) 43:1468–1478

Weber, et al., *Journal of Neurochemistry* (1985) 45:1541–1547.

Fukada, *Proc. Natl. Acad. Sci. USA* (1985) 82:8795–8799.

Manthorpe, et al., *Developmental Brain Research* (1986) 25:191–198.

Wallace, et al., *Brain Research* (1986) 375:92–101.

Gurney, et al., *Science* (1986) 234:566–574.

Watters, et al., *Journal of Neurochemistry* (1987) 49:705–713.

Unsicker, et al., *Proc. Natl. Acad. Sci. USA* (1987) 84:5459–5463.

Wallace, et al., *Brain Research* (1987) 411:351–363.

Dal Toso, et al., *The Journal of Neuroscience* (1988) 8:733–745.

McManaman, et al., *The Journal of Biological Chemistry* (1988) 263:5890–5897.

Anderson, et al., *Nature* (1988) 332:360–361.

*Primary Examiner*—Jeffrey E. Russel
*Attorney, Agent, or Firm*—Barbara Rea-Venter

[57] ABSTRACT

Novel neutrotrophic factor compositions are provided, obtained from lung tissue. The factors are found to be active on parasympathetic ganglion neutrons enhancing acetylcholine activity. The compositions find use in the treatment of a number of eye disorders.

8 Claims, No Drawings

NEUROTROPHIC FACTOR

INTRODUCTION

Technical Field

The invention relates to neurotrophic factors useful in treating neurodegenerative diseases affecting the ciliary ganglion. The factors find use in maintaining viability of parasympathetic neurons and enhancing acetylcholine formation in certain eye diseases.

Background

Neurotrophic factors are believed to be elaborated by target tissues, taken up into nerve terminals, and then transported retrogradely to neuronal cell bodies. Neurons are dependent on neurotrophic factors (NTF's) for survival and/or function, and many NTF's are thought to exist, each directed against a specific neuronal type or several types. While the NTF's are usually produced in extraordinarily small quantities by target tissues, several putative NTF's have been at least partially purified and shown to possess survival-promoting effects in vitro.

A mutually beneficial, reciprocal relationship exists between the target tissue and neuron. While the target tissue supplies NTF's for neurons, the neurons also provide trophic support and regulate the function of the target tissue. Indeed, in many cases and in clinical disorders, when the neurons die there is atrophy and loss of function of the target tissue. Thus, exogenously applied NTF's not only would directly support the survival and function of neurons, but also indirectly beneficially support or alter the function of the target tissue.

There are ocular diseases that may benefit from the activities of NTF's. For example, glaucoma is a disease characterized by an increase in intraocular pressure, cupping of the optic nerve head, and loss of visual field. Insufficient cholinergic innervation of the ciliary muscle in the eye may contribute to the decreased outflow of aqueous humor resulting in elevated intraocular pressure. At the present time, the condition is treated with anticholinesterases and parasympathomimetics. Therefore, enhancement of endogenous cholinergic tone by NTF's could be an effective therapy. Cholinergic innervation of the ciliary muscle originates in the ciliary ganglion. Stimulation of acetylcholine (muscarinic) receptors results in contraction of the ciliary muscle, decreased outflow resistance, and decreased intraocular pressure. Thus if NTF's could be used to stimulate acetylcholine receptors indirectly, for example by enhancing production of acetylcholine, the ciliary muscle would contract more forcefully, thereby enhancing outflow. Other diseases of the eye which may benefit from enhanced activation of the parasympathetic nerves by treatment with NTF include Adie's syndrome, dry eye, presbyopia, disorders of lacrimation, corneal wound disorders, and the like.

In view of the fact that there seem to be a large number of different neurotrophic growth factors, which appear to have different characteristics and different properties somewhat analogous to the sequence of interleukins, it is of great interest to be able to identify all of the naturally occurring NTF's, characterize them as to their physiological activities, either individually or in combination, and determine their utility in treating a wide variety of symptoms, syndromes, and diseases.

Relevant Literature

Levi-Montalcini, Science (1987) 237:1154-1162 provides an excellent review of nerve growth factor. Articles concerned with NTF's, including isolation, purification, and bioassays, include Barde et al., *EMBO. J.* (1982) 1:549-553; Gospodarowicz et al., *Proc. Natl. Acad. Sci. USA* (1984) 81:6963-6967; Barbin, *J. Neurochem.* (1984) 43:1468-1478; Weber et al., ibid. (1985) 1541-1547; Fukada, *Proc. Natl. Acad. Sci. USA* (1985) 82:8795-8799; Manthorpe et al., *Developmental Brain Research* (1986) 25:191-198; Wallace and Johnson, *Brain Research* (1986) 375:92-101; Gurney et al., *Science* (1986) 234:566-574; Watters and Hendry, *J. Neurochem.* (1987) 49:705-713; Unsicker, *Proc. Natl. Acad. Sci. USA,* (1987) 84:5459-5463; Wallace and Johnson, *Brain Research* (1987) 411:351-363; Dal Toso et al., *J. Neurosci.* (1988) 8:733-745; McManaman, *J. Biol. Chem.* (1988) 263:5890-5897; and Anderson et al., *Nature* (1988) 332:360-361. Also of interest is EPA Serial No. 0 233 838, entitled "Neurite-Promoting Factor and Process for the Manufacture Thereof".

SUMMARY OF THE INVENTION

Novel neurotrophic growth factor compositions are provided in substantially pure form, finding use as pharmaceutical compositions in therapy. The compositions find use in treating disorders which may be associated with ocular function associated with acetylcholine receptor activation, neuronal viability, maintenance of normal target organ function following nerve damage or degeneration, as well as other symptoms and diseases associated with ciliary ganglion and parasympathetic neuron function.

DESCRIPTION OF THE SPECIFIC EMBODIMENTS

In accordance with the subject invention, novel NTF compositions are provided of high purity. The NTF's are proteinaceous compositions which are characterized by having a pI in the range of 5.6 to 7.0, and a molecular weight of about 31.5 kD, as determined by SDS gel electrophoresis using known proteins as the standards. The subject composition may be obtained from any mammal, including primate, bovine, equine, porcine, lagomorpha, canine, feline, etc. In the subject invention porcine NTF is exemplified.

The subject NTF may be obtained in a variety of ways. The NTF may be extracted from lung tissue by an initial gross separation of homogenized lungs in a TRIS-HCl buffer, pH ~7.0, where the concentration of buffer will be about 1 to 20 mM. After separating the liquid from the particulate matter and delipidating the liquid phase, the liquid phase may then be fractionated on a size-separation type column, e.g., a S400 Sephacryl HR column, employing the same buffer as before with fractions taken from the void volume to approximately a 40 kD molecular weight range. Futher purification can be achieved on a preparative anion-exchange column, e.g., a DEAE HPLC column, employing the same buffer and using a linear NaCl gradient in the range of about 50 to 350 mM, where the active factor elutes between 100 and 250 mM NaCl. Possible heparin binding growth factors are removed by passing the active fractions from the DEAE HPLC column over a heparin affinity HPLC column. The NTF fraction does not bind to the heparin column. After adjusting to pH 5.6 the active fraction that did not bind to the heparin column, the factor is further purified using an analytical SP HPLC column equilibrated with 10 to 50 mM MES buffer, pH 5.6, followed by using a step gradient of NaCl where the factor elutes between 250 and 500 mM NaCl. The active fractions are then further purified by employing a molecular sieving HPLC column where the factor elutes in the 15 to 25 kD molecular weight range using a 10 to 15 mM MES buffer, pH 6.8 plus 350 to 750 mM NaCl, particularly 500 mM NaCl. SDS electrophoresis of the active fractions derived from the molecular sieving column provides a single silver-stained band at approximately 31.5 kD.

Rather than isolate the subject factor from natural sources, the factor may be prepared by recombinant techniques. The subject factor may be used to prepare monoclonal antibodies in accordance with conventional ways. See for example, U.S. Pat. Nos. 4,716,111; 4,716,117 and 4,713,325, and references cited therein. Using conventional techniques described by Stratagene, or others, the cells may be lysed and the mRNA of the lung cells reverse transcribed. The resulting DNA may then be inserted into an appropriate expression library such as a λgtll library, which is transformed into *E. coli* cells. The resulting fused proteins may then be screened with the monoclonal antibodies prepared from the subject NTF. The various colonies may then be screened with the subject antibody for proteins specifically binding to the subject monoclonal antibodies. Those clones may be used as probes for identifying specific mRNA using Northern analysis and the resulting mRNA reverse transcribed, cloned and sequenced to identify the specific sequence. In addition the subject NTF protein may also be sequenced, either partially or completely, so that the sequence of the NTF protein can be compared to the sequence encoded by the mRNA. Once having isolated the cDNA gene, the gene may then be used for expression in any convenient host, either prokaryotic or eukaryotic. There are an ample number of expression systems in the literature; see, for example, Maniatis et al., *A Laboratory Manual*, Cold Spring Harbor, N.Y., 1982.

The subject compositions are shown to have a number of physiological activities, as evidenced by in vitro bioassays. The substance is capable of maintaining viable embryonic chicken ciliary neurons in vitro. The subject compositions also increase choline acetyltransferase activity in parasympathetic ciliary neurons in culture. The increase in choline acetyltransferase activity can be enhanced by the presence of KCl in from about 5 to 50 mM KCl, with the activity increasing linearly within that range. A number of other salts do not show the same stimulation. The subject compositions have a $ED_{50}$ of at least 25 ng/ml, preferably at least about 50 ng/ml based on the bioassay described in the experimental section. In addition, the purification achieves at least a 15,000-fold increase in activity over the supernatant.

The subject compositions can find use with a number of disorders associated with the eye, where the disorders are related to the inadequate functioning of ciliary ganglion and parasympathetic nerve cells or of the tissues innervated by the ciliary ganglia.

One disorder that may be treated with NTF is glaucoma. By stimulating or raising the level of choline acetyltransferase, the increase in amount of acetylcholine released by post-ganglionic nerve terminals innervating the ciliary body may be accompanied by an increase in the number of synapses and acetylcholine release in these tissues. This enhanced cholinergic tone in the ciliary muscle would provide for a reduction in intraocular pressure. By preventing the death of ciliary ganglion neurons, the subject compounds would be useful in the treatment of Adie's syndrome and presbyopia. By virtue of the ability to stimulate parasympathetic ganglion-mediated lacrimal secretion, the subject compositions could be used in the treatment of disorders of lacrimation or in corneal-wound disorders.

The subject formulations for therapy are prepared in physiologically acceptable media such as saline, PBS, or balanced salt solution. The subject compositions are administered at different levels, depending on the disorder, the solution, the frequency of treatment, the severity of the disorder, and the like. Levels of treatment will generally be in the range of analogous factors, e.g. about 0.1-5 mg/kg. Administration are by injection, transdermal or transscleral delivery or other suitable method.

The following examples are offered by way of illustration and not by way of limitation.

EXPERIMENTAL

Purification Steps of the Factor

Step 1:

Fresh or partially thawed pig lungs (no strain preference) were homogenized in 2 vol (w/v) of 10 mM tris-HCl buffer, pH 7 in a Waring blender. The homogenate was centrifuged at 25,000×g for 60 min and the supernatant fraction was delipidated by passing it through gauze. The delipidated 25,000×g supernatant fraction was frozen, then thawed, and recentrifuged using the same conditions.

Step 2:

The twice-centrifuged 25,000×g supernatant fraction was loaded onto an S400 Sephacryl HR (Pharmacia) column previously equilibrated in 10 mM tris-HCl buffer, pH 7. Active fractions were taken from the void volume to approximately a 40 kD molecular weight range.

Step 3:

Active fractions derived from the Sephacryl column were loaded onto a preparative DEAE HPLC column that had previously been equilibrated with 10 mM tris-HCl buffer, pH 7 and the column was washed with the same buffer. Using a linear NaCl gradient, the factor eluted between 100 mM and 250 mM NaCl.

Step 4:

Active fractions derived from the DEAE HPLC column were loaded onto a heparin affinity HPLC column previously equilibrated with 10 mM MES buffer, pH 7. The column was washed with the same buffer. Over 98% of the NTF activity does not bind to the heparin column, that is, passes through the column while loading or with the buffer wash. If the NTF activity that did not bind to the heparin HPLC column the first time was loaded onto the heparin HPLC column again, it still did not bind, indicating that the heparin binding capacity of the column had not been exceeded. This step effectively removes heparin binding growth factors, such as acidic or basic fibroblast growth factor, which have been shown by other investigators to maintain the survival of ciliary ganglion neurons.

Step 5:

The pH of the active fraction that did not bind to the heparin HPLC column was adjusted to pH 5.6 and the active fraction was then loaded onto an analytical SP HPLC column that had previously been equilibrated with 25 mM MES buffer, pH 5.6. The column was washed with this same buffer. Using a step gradient of NaCl, the factor eluted between 250 mM and 500 mM NaCl.

Step 6:

Active fractions from the SP column were applied to a molecular sieving HPLC column and the factor eluted in the 12 kD to 25 kD molecular weight range using 25 mM MES buffer, pH 6.8+500 mM NaCl.

SDS electrophoresis of the active fractions derived from the molecular sieving HPLC column revealed a silver-stained band at approximately 31.5 kD.

Bioassay of the Factor

Fractions derived from chromatographic columns were assayed on embryonic day 8 chicken ciliary neurons. The neurons were incubated on a single layer of rat tail collagen in Eagle's minimum essential medium containing 10% fetal bovine serum, antibiotics, and the chromatographic fraction. The tissue culture plates were then placed in a 95% air, 5% $CO_2$ environment at 37° C. After 2 days in culture, surviving neurons were quantitated using the vital dye MTT (3-[4,5-dimethyl-thiazol-2-yl]-2,5-diphenyltetrazolium bromide) (see Manthorpe et al., *Dev. Brain Res.* (1986) 25:191-198.) MTT was taken up and converted into a large blue crystal if the neuron was alive. The living neurons were counted using a phase contrast objective on the microscope, 36 hrs after adding the MTT. Negative control wells contained the same tissue culture medium, but instead of a chromatography fraction, they received the buffer (e.g., tris buffer) used to elute the fractions from the chromatography column. Using this procedure, all of the control neurons were dead after two days, whereas the neurons in those wells that received chromatographic fractions containing the factor were alive.

In order to demonstrate the effectiveness of the subject compositions for restoration of innervation of the ciliary muscle and circular muscle of the eye, the following study is carried out:

Two groups of four cats are subjected to unilateral, surgical section of the post-ganglionic ciliary nerves. Outflow facility and pupil diameter are determined bi-laterally before and after the procedure to establish success of the surgery. One group of cats is treated daily with the subject NTF (1 mg/kg in PBS), while the other group of cats is treated only with the buffer. Changes in pupil diameter are determined daily, while outflow facility is measured every other day until restoration of ocular function occurs.

Tear break-up time and tear meniscus height are measured non-invasively with a slit lamp in unilaterally denervated cats. Lacrimation is also quantitated using the Schirmer test, consisting of hooking a strip of filter paper over the lid margin and measuring the length of wetting that occurs. Changes in tear composition are measured. Alterations in tear composition are measured as changes in the tear ions, protein, fatty acid, cholesterol ester, lecithin or polysaccharide concentrations. See, for example, Roherts and Erickson (1962) *J. Small Anim. Pract.* 3:1; Roberts (1962) *Mod. Vet. Pract.* 43:37. Time to restoration of normal lacrimal function is chronicled and compared between the use of the subject NTF and buffer.

Epithelial wound closure is measured in cats following the creation of a 4 mm central corneal abrasion. Wounds are stained with fluorescein and photographed, and wound radius determined. The parameters of wound closure, latency and rate of epithelial migration is determined from plots of wound radius versus time. See Crosson et al., *Ophthalmol. Vis. Sci.* (1986) 27:464-473. Denervated control cats are compared to normal cats and denervated cats treated with NTF. Epithelial barrier functions in denervated and treated cats are assessed by measuring the total trans-epithelial and paracellular resistance by standard electrophysiological techniques. (See Crosson et al., *Ophthalmol. Vis. Sci.* (1984) 27:1240-1245 and Marshall et al., *J. Membrane Biol.* (1983) 73:275-282.)

In accordance with the subject invention, novel compositions are provided for treatment of ocular disorders associated with ciliary ganglionic nerve cell degeneration. The subject compositions are highly purified and can be obtained by extraction of mammalian lung tissue. The subject compositions provide for an alternative treatment for various disorders which are treated only with difficulty today or for which no useful treatment exists.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A composition comprising a neurotropic factor characterized by:

an $ED_{50}$ of at least about 25 ng/ml as measured in vitro using embryonic day 8 chicken ciliary neurons;

a pI in the range of 5.6-7.0;

a molecular weight as determined by SDS gel electrophoresis of obtainable from mammalian lung tissue;

capable of maintaining viable embryonic ciliary neurons in vitro, as compared to the absence of said composition;

capable of increasing choline acetylatransferase activity in parasympathetic ciliary neurons in culture, wherein said increasing is reponsive to changes in potassium ion concentration;

and does not bind heparin.

2. A composition according to claim 1, wherein said composition is concentrated in said neurotrophic factor by at least one an anionic, cationic and molecular sieving HPLC columns.

3. A composition according to claim 1, wherein said composition is at least substantially pure.

4. A composition according to claim 1, wherein said neurotrophic factor is isolated from pig lung.

5. A composition according to claim 1, obtained by the method of:

homogenizing lungs and separating to provide a supernatant;

separating said supernatant into fractions on a molecular sieving column by eluting with a buffer at about pH 7 to provide a first active fraction;

separating said first active fraction with an anionic exchange column eluting with a linear salt gradient to obtain a second active fraction eluting between 100 mM and 250 mM;

loading the second active fraction onto a heparin affinity HPLC column and collecting a third active fraction that does not bind to the heparin column;

adjusting said third active fraction to about pH 5.6 and separating with an analytical cationic exchange column using a step salt gradient and isolating a fourth active fraction eluting between 250 mM and 500 mM; and separating said fourth active fraction with a molecular sieving HPLC column using 25 mM MES buffer, pH 6.8, 500 mM NaCl to provide a fraction eluting in the 15 kD to 25 kD molecular weight range consisting of a said composition.

6. A method for producing a composition according to claim 1 comprising:

homogenizing lungs and separating to provide a supernatant;

separating said supernatant into fractions on a molecular sieving column by eluting with a buffer at about pH 7 to provide a first active fraction;

separating said first active fraction with an anionic exchange column eluting with a linear salt gradient to obtain a second active fraction eluting between 100 mM and 250 mM;

loading the second active fraction onto a heparin affinity HPLC column and collecting a third active fraction that does not bind to the heparin column;

adjusting said third active fraction to about pH 5.6 and separating with an analytical cationic exchange column using a step salt gradient and isolating a fourth active fraction eluting between 250 mM and 500 mM; and separating said fourth active fraction with a molecular sieving HPLC column using 25 mM MES buffer, pH 6.8, 500 mM NaCl to provide a fraction eluting in the 15 kD to 25 kD molecular weight range consisting of said composition.

7. A composition according to claim 1, wherein said $ED_{50}$ is at least 50 ng/ml as measured in vitro using embryonic day 8 chicken ciliary neurons.

8. A composition according to claim 3, wherein said composition provides a single silver-stained band at approximately 31.5 kD using SDS electrophoresis.

* * * * *

UNITED STATES PATENT AND TRADEMARK OFFICE
CERTIFICATE OF CORRECTION

PATENT NO. : 5,166,317
DATED : November 24, 1992
INVENTOR(S) : Wallace

It is certified that error appears in the above-indentified patent and that said Letters Patent is hereby corrected as shown below:

On the title page, Item [75] Inventors, delete "David E. Potter; Craig E. Crosson, all"

On the title page, Under Attorney, Agent, or Firm:

"Rea-Venter' should be --Rae-Venter--.

Column 6, line 44, after "electrophoresis of" add --about 31.5 KD;--
Column 6, line 56, "an" should be --of--.

Signed and Sealed this

Fourth Day of January, 1994

Attest:

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,166,317
DATED : November 24, 1992
INVENTOR(S) : Thomas L. Wallace et al.

It is certified that error appears in the above-indentified patent and that said Letters Patent is hereby corrected as shown below:

On the title page, item [57], line 3, please replace "neutrons" with --neurons--.

Signed and Sealed this

Twelfth Day of July, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,166,317
DATED : November 24, 1992
INVENTOR(S) : Wallace, et al.

It is certified that error appears in the above-indentified patent and that said Letters Patent is hereby corrected as shown below:

At column 3, line 49, after "KCI in" insert --concentrations ranging from--.

Col. 6, Claim 1, line 49, delete "acetylatransferase" and insert --acetyltransferase--.

Claim 7, lines 18-20, delete "according to claim 1, wherein said $ED_{50}$ is at least 50 ng/ml as measured in vitro using embryonic day 8 chicken ciliary neurons" and insert --comprising a neurotrophic factor characterized by: an $ED_{50}$ of at least 50 ng/ml as measured in vitro using embryonic day 8 chicken ciliary neurons;
a pI in the range of 5.6-7.0;

UNITED STATES PATENT AND TRADEMARK OFFICE
CERTIFICATE OF CORRECTION

PATENT NO. : 5,166,317
DATED : November 24, 1992
INVENTOR(S) : Wallace, et al.

It is certified that error appears in the above-indentified patent and that said Letters Patent is hereby corrected as shown below:

a molecular weight as determined by SDS gel electrophoresis of about 31.5 kD; obtainable from mammalian lung tissue; capable of maintaining viable embryonic ciliary neurons in vitro, as compared to the absence of said composition; capable of increasing choline acetyltransferase activity in parasympathetic ciliary neurons in culture, wherein said increasing is responsive to changes in potassium ion concentration; and does not bind heparin--.

Signed and Sealed this

Eleventh Day of February, 1997

Attest:

BRUCE LEHMAN

Attesting Officer

Commissioner of Patents and Trademarks